United States Patent [19]

Hyatt et al.

[11] Patent Number: 5,294,703
[45] Date of Patent: Mar. 15, 1994

[54] PROCESS FOR PREPARING α-D-CELLOBIOSE OCTAACETATE

[75] Inventors: John A. Hyatt, Kingsport, Tenn.; Tony L. Sander, Batesville, Ark.; D. Mark Naylor, Kingsport; Bobby L. Bernard, Rogersville, both of Tenn.

[73] Assignee: Eastman Kodak Company, Rochester, N.Y.

[21] Appl. No.: 44,344

[22] Filed: Apr. 7, 1993

Related U.S. Application Data

[63] Continuation-in-part of Ser. No. 877,634, May 1, 1992, abandoned.

[51] Int. Cl.$^5$ .................... C07H 1/00; C07H 15/24; C08B 3/06; C08B 15/00
[52] U.S. Cl. ........................... 536/119; 536/5; 536/6; 536/6.1; 536/69; 536/70; 536/71; 536/72; 536/73; 536/74; 536/75; 536/76; 536/79; 536/80; 536/81; 536/82; 536/83
[58] Field of Search .............. 536/119, 5, 6, 6.1, 536/69, 76, 79, 80, 81, 82, 83, 70, 71, 72, 73, 74, 75

[56] References Cited

U.S. PATENT DOCUMENTS

| | | | |
|---|---|---|---|
| 4,602,003 | 7/1986 | Malinow | 514/26 |
| 4,602,005 | 7/1986 | Malinow | 514/26 |
| 5,010,185 | 4/1991 | Urban | 536/6.1 |
| 5,142,034 | 8/1992 | Bellas et al. | 536/80 |

FOREIGN PATENT DOCUMENTS 0403150 12/1990 European Pat. Off. .

OTHER PUBLICATIONS

Uber die Cellobiose und die Acetolyse der Cellulose, Wilhelm Schliemann, Ann. 378, pp. 366–381 (1911).
Klein, *Z. Angew, Chem.* 25, pp. 1409–1423 (1912).
Maquenne and Goodwin, *Bull. Soc. Chim. France*, vol. 31, pp. 854–859 (1904).
Zur Kenntnis der Cellulose, Karl Freudenberg, Chem. Ber., vol. 54, pp. 767–772 (1921).
Franchimont, *Chem. Ber.* Vol. 12, pp. 1938–1942 (1879).
Ost. *Liebigs* Ann Chim. 378, pp. 313–343 (1913).
Uber die Cellobiose Zd. H. Straup, w.M.k. Akad. und J. Konig *Monatsh*, vol. 22, pp. 1011–1036 (1901).
Organic Syntheses, vol. 2, A Revised Edition of Annual Volumnes X–XIX, edited by A. H. Blatt, 3rd printing, NY., N.Y., John Wiley & Sons, Inc. pp. 124–126 (1943).
Ind. Eng. Chem., Prod. Res. Develop., vol. 1, No. 4, Dec., 1962, pp. 285–287, P. E. Robbins et al., "Synthesis of Cellobiose Octaacetate".

*Primary Examiner*—Ronald W. Griffin
*Attorney, Agent, or Firm*—Bernard J. Graves, Jr.; William P. Heath, Jr.

[57] ABSTRACT

Provided is a novel improved process for the preparation of α-D-cellobiose octaacetate via the acetylative degradation of cellulose or cellulose acetate. The title compound is provided in high yield and quality in a facile one-pot process, amenable to large-scale synthesis.

22 Claims, No Drawings

PROCESS FOR PREPARING α-D-CELLOBIOSE OCTAACETATE

CROSS REFERENCE TO RELATED APPLICATION

This application is a continuation-in-part of U.S. Ser. No. 07/877,634, filed May 1, 1992, now abandoned, incorporated herein by reference.

1. Field of the Invention

This invention belongs to the field of synthetic organic chemistry. In particular, this invention relates to an improved process for the preparation of α-D-cellobiose octaacetate.

2. Background of the Invention

α-D-Cellobiose octaacetate is known to be useful in the synthesis of certain pharmaceutical agents employing the β-cellobioside moiety to provide a prodrug. For example, U.S. Pat. Nos. 4,602,003 and 4,602,005, incorporated herein by reference describe Tigogenin β-cellobioside as a compound useful in the treatment of hypercholesterolemia and atherosclerosis. These references describe two different syntheses for the final compound via β-cellobiose octaacetate.

The most recent published description of the preparation of α-cellobiose octaacetate is that of G. Braun, in *Organic Syntheses*, Collective Volume II, p. 124, Wiley, N.Y., 1943. In the Braun synthesis, 400 mL of acetic anhydride is treated with 36 mL of sulfuric acid. To this mixture is added 100 g of cellulose (i.e., cotton) with control of the resulting exotherm at 45°–55° C. The reaction mixture is then held at 35° C. for seven days. Seeding the reaction mixture is considered optional by Braun; he reports that the title compound begins to crystallize from the reaction mixture in the second day of the reaction period. After seven days, the reaction mixture is poured into 20 L of water and the resulting precipitate isolated by filtration. This crude product (which we have found by high performance liquid chromatographic analysis to be about 52% of the desired product, the remainder being glucose pentaacetate and higher oligosaccharide peracetates) is then reslurried in warm methanol to give the title compound of better purity; this product is finally recrystallized from methanol/chloroform to yield 65-69 g of the title compound having $[\alpha]_D = +41.6°$, mp=220°-222° C.

SUMMARY OF THE INVENTION

The present invention provides an improved facile one step process for the preparation of α-D-cellobiose octaacetate via acetylative degradation of cellulose. The process of the present invention overcomes inherent difficulties in prior art processes, i.e., in reaction time and reaction volume.

DETAILED DESCRIPTION OF THE INVENTION

The present invention provides an improved process for the preparation of α-D-cellobiose octaacetate (1)

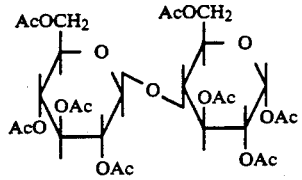

wherein Ac is acetyl, by the acetylative degradation of cellulose. In particular, the present invention provides an improved process for preparing α-D-cellobiose octaacetate which comprises the steps:

(a) treating cellulose or cellulose acetate with a mixture of acetic anhydride, acetic acid, and a strong acid, while maintaining the mixture at a temperature of below about 80° C.;

(b) heating the mixture at about 35° to 65° C. for about 8 to 36 hours;

(c) adding at least a sufficient amount of a $C_1$–$C_5$ alcohol to quench any remaining unreacted acetic anhydride; followed by (d) isolation of α-D-cellobiose octaacetate.

In the above process, it is preferred that the reactants comprise, for each 100 parts (by weight) of cellulose, 200-400 parts acetic anhydride, 50-200 parts acetic acid, and 10-70 parts of a strong acid. In this regard, the term "strong acid" preferably refers to an acid such as sulfuric, methanesulfonic, trichloromethanesulfonic, chlorosulfonic, trifluoromethanesulfonic acid, and the like. The cellulose starting material can be obtained by any of the well-known botanical or bacterial methods.

In the above process, it is preferred that the reaction mixture be heated and agitated, e.g., stirred, for 8-36 hours, at 35°-65° C. It is further preferred that the reaction is conducted at a temperature of about 45°-55° C., most preferably at about 50° C. The reaction time is preferably about 14-20 hours, most preferably about 18 hours. In the work-up of the reaction mixture, a $C_1$–$C_5$ alcohol, preferably methanol, is utilized in at least an amount sufficient to quench any remaining acetic anhydride. Preferably an excess of methanol is used. This utilization of a $C_1$–$C_5$ alcohol overcomes the necessity of a large-volume, cumbersome work-up procedure as taught by Braun. It is preferred that a 50-300 parts be added at a temperature of less than about 30° C. The resulting product can then be isolated via filtration or centrifugation.

Finally, it is also preferred that seed crystals of α-D-cellobiose octaacetate be added during the initial stages of the reaction.

Thus, it will be appreciated that the improved process of the present invention overcomes two major drawbacks of the Braun synthesis referred to above, i.e., reaction volume and reaction time. Other attempts to avoid the large reaction volumes have resulted in even longer reaction times (see Pringshiem and Merkatz, *Z. Physiol. Chem.*, 25, 1409 (1912)).

As to the improvement in reaction time, merely increasing the temperature is not the solution. In our experiments, raising the temperature to 50° C., while employing the other elements/steps of the Braun procedure combined with a methanol quench resulted in a virtually unfilterable slurry.

In addition, the present invention allows the substitution of cellulose acetate for cellulose as a raw material feedstock. This in effect means that acetylation of at least some of the cellulose hydroxyls can take place prior to degradation of the cellulose chain to cellobiose acetate. We find that the yield of product 1 is slightly greater when cellulose acetate is used instead of cellulose as the feedstock; however in the case of cellulose acetate feedstock, a somewhat longer reaction time is generally required.

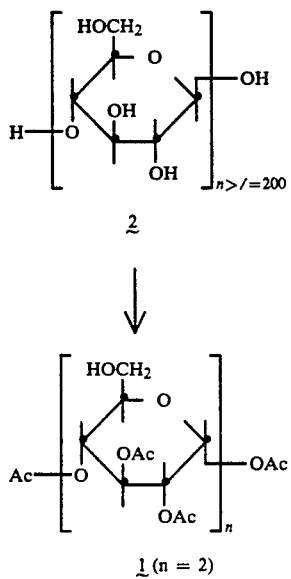

Thus, one can preferably prepare the title compound from cellulose acetate as follows:

A mixture of 442 mL of acetic anhydride, 725 mL of acetic acid, and 115 mL of sulfuric acid is stirred at 44° C. To this mixture is added 544 g of cellulose acetate (Eastman Chemical Company commercial CA-398-30, with a degree of acetylation of 2.45 acetyl groups per glucose repeat unit). The mixture is then preferably seeded with a small amount of 1 and stirred at 48°-52° C. for 30 hours. The mixture is cooled, treated with an alcohol such as methanol, and worked up as described above to afford the desired compound.

Thus, as a further aspect of the present invention, there is provided a process for preparing α-D-cellobiose octaacetate which comprises the steps:

(a) treating cellulose acetate with a mixture of acetic anhydride, acetic acid, and a strong acid, while maintaining the mixture at a temperature of below about 80° C.;

(b) heating the mixture at about 48° to 52° C. for about 20 to 35 hours; and (c) cooling to a temperature of about 15° to about 25° C.;

(d) adding at least a sufficient amount of a $C_1$–$C_5$ alcohol to quench any remaining unreacted acetic anhydride; followed by (e) isolation of α-D-cellobiose octaacetate.

In a preferred embodiment of this aspect of the present invention, there is provided a process for preparing α-D-cellobiose octaacetate which comprises the steps:

(a) treating cellulose acetate with a mixture of acetic anhydride, acetic acid, and a strong acid, while maintaining the mixture at a temperature of below about 80° C.;

(b) adding seed crystals of α-D-cellobiose octaacetate to said mixture while heating the mixture from about 35° to 65° C. for about 8 to 36 hours;

(c) cooling the mixture to from about 0° to about 30° C.; and (d) adding at least a sufficient amount of a $C_1$–$C_5$ alcohol to quench any remaining unreacted acetic anhydride; followed by (e) isolation of α-D-cellobiose octaacetate.

EXPERIMENTAL SECTION

Preparation of α-D-cellobiose Octaacetate from Cellulose

A 12 L flask was equipped with stirrer, addition funnel, reflux condenser, thermometer, and was arranged for water-bath cooling or mantle-heating. The flask was charged with 3132 mL of acetic anhydride and 1044 mL of glacial acetic acid. Stirring was commenced and there was added in a slow stream over 18 minutes 376 mL of 98-100% sulfuric acid. During this addition, the mixture exothermed from 25° C. to 54° C. There was then added 1044 g of Placetate (ITT Rayonier) wood pulp cellulose over 45 minutes. Water-bath cooling was used to control the reaction temperature between 50° and 56° C.; temperature was easily regulated by controlling the addition rate. The reaction mixture passed through a thick yellow slurry stage, and shortly after the end of the addition became a thin yellow solution containing some particulates. The cooling bath was replaced with a heating mantle and the temperature of the mixture was adjusted to 50°-52° C. One hour after completion of the addition of the cellulose, there was added in one portion 8.0 g of α-D-cellobiose octaacetate seed crystals. Five hours later an additional 8 g of α-D-cellobiose octaacetate seed crystals was added. Stirring was continued at 50°-52° C. for a total of 18 hours after completion of the cellulose addition. At this time the mix was a dark mauve slurry. After 18 hours, the mantle was replaced with a cold water bath and the mix cooled to 17° C. A 3 L portion of methanol was then added at such a rate that the pot temperature did not exceed 35° C. (An exotherm occurred during the addition of the first 500 mL of methanol-total addition time was 35 minutes). The mixture was then re-cooled to 17° C. and filtered on a 24-cm Buchner funnel. Filtration required about 40 minutes, and was followed by washing of the cake with 2.6 L of methanol, which required an additional 30 minutes. The resulting white product was air-dried overnight to provide 788 g of the title compound.

Mp=200°-204° C. (decomposition)

$[\alpha]^{22}_D$, +40.5° (CHCL$_3$)

HPLC assay—99% pure

Sulfur analysis—1005 ppm $^1$H NMR* (300 MHz) delta 6.24 (d, j=4, 1H), 5.43(t, j=8, 1H), 5.2–4.9(m, 13 lines, 4H), 4.6–4.3(m, 8 lines, 3H), 4.2–3.9(m 8 lines, 3H), 3.8(t, j=9, 1H), 3.7–4.6 (br m, 1H), 2.18 (s, 3H), 2.12 (s, 3H), 2.08 (s, 3H), 2.04, (s, 3H), 2.03 (s, 3H), 2.01 (s, 3H), 2.00 (s, 3H), 1.98 (s, 3H).

IR* (cm$^{-1}$) (mineral oil mull): 1750, 1230, 1168, 1142, 1110. 1042, 1110. 1041, 949, 921, 908 cm$^{-1}$.

*(identical to an authentic sample of α-D-cellobiose octaacetate)

Analysis calculated for $C_{28}H_{38}O_{19}$: C, 49.3; H, 5.47%; Found C, 49.6; H, 5.68%.

Preparation of α-D-Cellobiose Octaacetate from Cellulose Acetate

To a nitrogen purged, 3-liter, three-necked, round-bottomed flask, equipped with a stirrer, addition funnel, reflux condenser, thermometer, a heating mantle, and a cooling bath, was added 442 mL (4.68 mol) of acetic anhydride and 375 mL of acetic acid at 25° C. Sulfuric acid (115 mL; 2.07 mol) was added to the reactor via dropping funnel, followed by an additional 350 mL of acetic acid. The reaction mixture was heated to 44° C. with rapid agitation. To the reaction mixture was added 544 g (2.05 mol) of cellulose acetate (CA- 398-30) through a funnel over one hour while maintaining the temperature at 48°-52° C. The funnel was then rinsed with 50 mL of acetic acid. At the end of the one hour and at two hours post-cellulose acetate addition, the reaction mixture is seeded with 4 g of α-D-cellobiose octaacetate. After 30 hours post-cellulose acetate addition, the reaction mixture was cooled to 18°-20° C. Methanol (1050 mL) was added, via dropping funnel, to the mixture while maintaining the temperature below 35° C. After stirring for 20 minutes at 20°-30° C., the mixture was filtered on a 18.5-cm Buchner funnel. The cake was washed with 1700 mL methanol and air dried overnight. The product analyzed 93–95% (HPLC) purity. Optical rotation, +40.5°, mp, 185° (dec). Yield, 284–288 g.

We claim:

1. A process for preparing α-D-cellobiose octaacetate which comprises the steps:
   (a) treating cellulose with a mixture of acetic anhydride, acetic acid, and a strong acid, while maintaining the mixture at a temperature of below about 80° C.;
   (b) heating the mixture at about 35° to 65° C. for about 8 to 36 hours; and
   (c) adding at least a sufficient amount of a $C_1$–$C_5$ alcohol to quench any remaining unreacted acetic anhydride; followed by
   (d) isolation of α-D-cellobiose octaacetate.

2. The process of claim 1, wherein the strong acid is selected from the group consisting of sulfuric, methanesulfonic, trichloromethanesulfonic, chlorosulfonic, and trifluoromethanesulfonic acid.

3. The process of claim 1, wherein the $C_1$–$C_5$ alcohol is selected from the group consisting of methanol, ethanol, n-propanol, i-propanol, and, n-butanol.

4. The process of claim 3, wherein the $C_1$–$C_5$ alcohol is methanol.

5. The process of claim 3, wherein the $C_1$–$C_5$ alcohol is ethanol.

6. The process of claim 3, wherein the $C_1$–$C_5$ alcohol is n-propanol.

7. The process of claim 3, wherein the $C_1$–$C_5$ alcohol is i-propanol.

8. A process for preparing α-D-cellobiose octaacetate which comprises the steps:
   (a) treating cellulose with a mixture of acetic anhydride, acetic acid, and a strong acid, while maintaining the mixture at a temperature of below about 80° C.;
   (b) adding seed crystals of α-D-cellobiose octaacetate to said mixture while heating the mixture from about 35° to 65° C. for about 8 to 36 hours;
   (c) cooling the mixture to from about 0° to about 30° C.; and
   (d) adding at least a sufficient amount of a $C_1$–$C_5$ alcohol to quench any remaining unreacted acetic anhydride; followed by
   (e) isolation of α-D-cellobiose octaacetate.

9. The process of claim 8, wherein the strong acid is selected from the group consisting of sulfuric, methanesulfonic, trichloromethanesulfonic, chlorosulfonic, and trifluoromethanesulfonic acid.

10. The process of claim 8, wherein the $C_1$–$C_5$ alcohol is selected from the group consisting of methanol, ethanol, n-propanol, i-propanol, and, n-butanol.

11. The process of claim 10, wherein the $C_1$–$C_5$ alcohol is methanol.

12. The process of claim 10, wherein the $C_1$–$C_5$ alcohol is ethanol.

13. The process of claim 10, wherein the $C_1$–$C_5$ alcohol is n-propanol.

14. The process of claim 10, wherein the $C_1$–$C_5$ alcohol is i-propanol.

15. A process for preparing α-D-cellobiose octaacetate which comprises the steps:
   (a) treating cellulose acetate with a mixture of acetic anhydride, acetic acid, and a strong acid, while maintaining the mixture at a temperature of below about 80° C.;
   (b) heating the mixture at about 48° to 52° C. for about 20 to 35 hours; and
   (c) cooling to a temperature of about 15° to about 25° C.;
   (d) adding at least a sufficient amount of a $C_1$–$C_5$ alcohol to quench any remaining unreacted acetic anhydride; followed by
   (e) isolation of α-D-cellobiose octaacetate.

16. The process of claim 15, wherein the strong acid is selected from the group consisting of sulfuric, methanesulfonic, trichloromethanesulfonic, chlorosulfonic, and trifluoromethanesulfonic acid.

17. The process of claim 15, wherein the $C_1$–$C_5$ alcohol is selected from the group consisting of methanol, ethanol, n-propanol, i-propanol, and, n-butanol.

18. The process of claim 17, wherein the $C_1$–$C_5$ alcohol is methanol.

19. A process for preparing α-D-cellobiose octaacetate which comprises the steps:
   (a) treating cellulose acetate with a mixture of acetic anhydride, acetic acid, and a strong acid, while maintaining the mixture at a temperature of below about 80° C.;
   (b) adding seed crystals of α-D-cellobiose octaacetate to said mixture while heating the mixture from about 35° to 65° C. for about 8 to 36 hours;
   (c) cooling the mixture to from about 0° to about 30° C.; and
   (d) adding at least a sufficient amount of a $C_1$–$C_5$ alcohol to quench any remaining unreacted acetic anhydride; followed by
   (e) isolation of α-D-cellobiose octaacetate.

20. The process of claim 19, wherein the strong acid is selected from the group consisting of sulfuric, methanesulfonic, trichloromethanesulfonic, chlorosulfonic, and trifluoromethanesulfonic acid.

21. The process of claim 19, wherein the $C_1$–$C_5$ alcohol is selected from the group consisting of methanol, ethanol, n-propanol, i-propanol, and, n-butanol.

22. The process of claim 21, wherein the $C_1$–$C_5$ alcohol is methanol.

* * * * *